US 6,734,668 B2

(12) United States Patent
Hils et al.

(10) Patent No.: US 6,734,668 B2
(45) Date of Patent: May 11, 2004

(54) EDDY CURRENT PROBE HAVING DIAGONAL MAGNETIC FIELDS ALTERNATING BETWEEN POSTS AT CORNERS OF ORTHOGONAL SOLENOID COILS

(75) Inventors: Christopher Hils, Redmond, WA (US); David Jonathan Brown, Enumclaw, WA (US)

(73) Assignee: Zetec, Inc., Issaquah, WA (US)

( * ) Notice: Subject to any disclaimer, the term of this patent is extended or adjusted under 35 U.S.C. 154(b) by 0 days.

(21) Appl. No.: 10/262,820

(22) Filed: Oct. 2, 2002

(65) Prior Publication Data

US 2004/0066191 A1 Apr. 8, 2004

(51) Int. Cl.[7] .................... G01N 27/90; G01N 27/82
(52) U.S. Cl. ............... 324/232; 324/238; 324/247
(58) Field of Search .................. 324/219–221, 324/232, 234–238, 247, 253, 146; 336/199, 208, 213, 221, 232

(56) References Cited

U.S. PATENT DOCUMENTS

| | | | | |
|---|---|---|---|---|
| 3,354,385 A | * | 11/1967 | Wood et al. | 324/234 |
| 3,495,166 A | * | 2/1970 | Lorenzi et al. | 324/238 |
| 4,204,159 A | * | 5/1980 | Sarian et al. | 324/232 |
| 4,292,589 A | * | 9/1981 | Bonner | 324/221 |
| 4,675,607 A | * | 6/1987 | Golker et al. | 324/247 |
| 6,181,130 B1 | * | 1/2001 | Hoshi et al. | 324/253 |

* cited by examiner

Primary Examiner—Jay Patidar
Assistant Examiner—Darrell Kinder
(74) Attorney, Agent, or Firm—David L. Tingey (57) ABSTRACT

An eddy current probe comprising two solenoid coils wound around a common rectangular wafer base of high permeability material extending beyond the coils at wafer corners with the wafer becoming the solenoid core. Posts also of high permeability material depend from a wafer front at its corners with coils crossing orthogonally on the wafer. The coils are connected to alternating current to produce magnetic fields that have like magnetic poles at wafer corners diagonally opposed across the wafer, the coils switching in phase to alternate the magnetic field between posts at base diagonal corners. With the posts at the wafer base corners, the combined magnetic fields generated from the orthogonal coils conduct through the posts and emanate from post ends. The post ends have a curvature matching that of a material to be tested for better coupling the magnetic field into the material. Thus, with posts ends positioned proximate a material to be tested, the combined magnet field is delivered to the test material without significant loss. A cap of high magnetic permeability can cover the base underside between posts in providing a guide to complete the magnetic circuit secondary magnetic fields that pass under the base instead of the primary magnetic circuit preferred between post ends.

16 Claims, 7 Drawing Sheets

EDDY CURRENT PROBE HAVING DIAGONAL MAGNETIC FIELDS ALTERNATING BETWEEN POSTS AT CORNERS OF ORTHOGONAL SOLENOID COILS

BACKGROUND

1. Field of the Invention

This invention relates to eddy current probes, and more specifically to a probe with orthogonal solenoid coils with the electromagnetic fields focused through posts.

2. Prior Art

It is known in the art that variations in conductivity and permeability of a material indicate the presence of structural defects such as cracks and corrosion. These variations can be measured by propagating a primary magnetic field into the material to create eddy currents. The eddy currents generated in the material then generate a return magnetic field that is detected by the probe coil. Defects in such materials that decrease the conductivity and disrupt the eddy currents cause the magnitude of the return magnetic field to decrease.

When the material is without flaws, the two magnetic fields are largely out of phase and the fields partially cancel, which reduces the coil voltage. Therefore, the probe coil voltage increases to indicate that the test coil is adjacent a defect. Signature characteristics of the flaw appear as a small modulation of the return magnetic field carrier signal. Thus, the sensitivity of the probe and the ability to sense the signature of the flaw is directly dependent on the magnitude of the incident primary magnetic field. It is therefore advantageous to have a maximum magnetic field strength.

SUMMARY OF THE INVENTION

An eddy current probe comprises two solenoid coils wound around a common rectangular wafer base of high permeability material extending beyond the coils at wafer base corners with the base becoming the solenoid core. Posts also of high permeability material depend from a base front at its corners.

A first coil wraps the base around first opposing base sides passing between pairs of the depending corner posts. A second coil wraps the base around second opposing base sides passing between different pairs of the depending corner posts, crossing the first coil orthogonally on the base front and back.

The coils are adapted to connect to alternating electric current such that magnetic fields generated by the two coils have like magnetic poles at base corners diagonally opposed across the base. Connection to electric current varies such that in a first condition the electric currents driving the two coils are in phase producing like magnetic poles at first diagonally opposing base corners. The connection in a second condition is such that the two coils are 180 degrees out of phase producing like magnetic poles instead at second opposing base corners separated circumferentially by the first opposing base corners. Thus, in the first condition, a combined magnetic field of the two solenoids crosses the base diagonally between the first opposing base corners. In the second condition, a second combined magnetic field crosses the base diagonally between the second opposing base corners orthogonal to the direction of the first combined magnetic field.

When the first combined magnetic field penetrates into a material to be tested, eddy currents are generated in the material in a first eddy current direction corresponding to the direction of the first combined magnetic field. The magnitude of eddy currents decreases significantly more for a material flaw not parallel with the eddy current direction than for a parallel flaw. Thus, by alternating between orthogonal first and second combined magnetic fields a flaw that might be less detectable as a result of a combined magnetic field in a first direction might be better detected by the other combined magnetic field in a direction orthogonal to the first.

The magnetic field generated by eddy currents generally in the material constitute a carrier signal that affects voltage in the orthogonal coils that is not dependent on magnetic field direction. Small changes in the eddy current magnetic field are modulations on the carrier signal. Subtracting the voltage signals in the respective coils therefore largely removes the carrier signal leaving mostly the change in eddy current signal due to a presence of a material anomaly.

The magnetic field strength decreases with distance from the solenoid. Therefore, it is advantageous to have the field source as close to the material to be tested as possible. The wafer base corners from which the combined magnetic fields emanate necessarily are separated from the test material at least by the thickness of the coils with the resulting decrease in magnetic field strength at the material. To direct the combined magnetic field from the solenoid to the test material with minimum loss of field strength, posts are located on the base corners from where the combined magnetic fields emerge from the two orthogonal coils. The combined magnetic fields are largely conducted through the posts and out post ends. The post ends are of length greater than the extent of the coils on the base and of sufficient length to place the post ends proximate the material to be tested, ideally located in near proximity to the material surface to minimize loss of field strength.

Post ends have a curvature matching a material to be tested to improve coupling of the magnetic field from the post into the test material. That is, for a flat test material, the post ends are flat; for a curved material such as a tube tested from its inside, the post ends are concave with a radius matching the inner radius of the test tube. Without a matching post end curvature, only an edge of the post is in near contact with the curved test material, the remaining post end being separated from the test material resulting in "lift off," a reduction of eddy current signal strength due to poor or inconsistent coupling of the magnetic field into the test material, a common cause of which is separation of the probe drive coils that excite eddy currents in the test material from the surface of the test material. Varying distance of the solenoid coil from the test material as the probe translates along the material also changes magnetic field strength coupled into the test material and hence the magnitude of eddy currents generated by the magnetic field. These changes in the eddy current signal while actually caused only by varying lift off may be interpreted as a material flaw. Therefore it is advantageous to have the post ends consistently and uniformly riding on the test material surface or at least a close measured distance from the material with post end curvature matching test material curvature.

DETAILED DESCRIPTION OF THE PREFERRED EMBODIMENT

Figure 1:
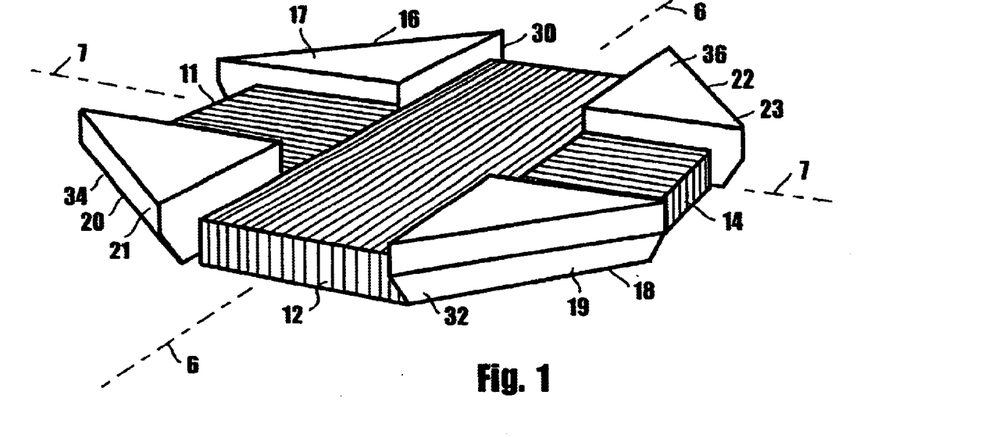
FIG. 1 is a perspective view of the eddy current probe of the present invention showing orthogonal coils wound around a common base between magnetic field directing posts on extended base corners.
Figure 2:
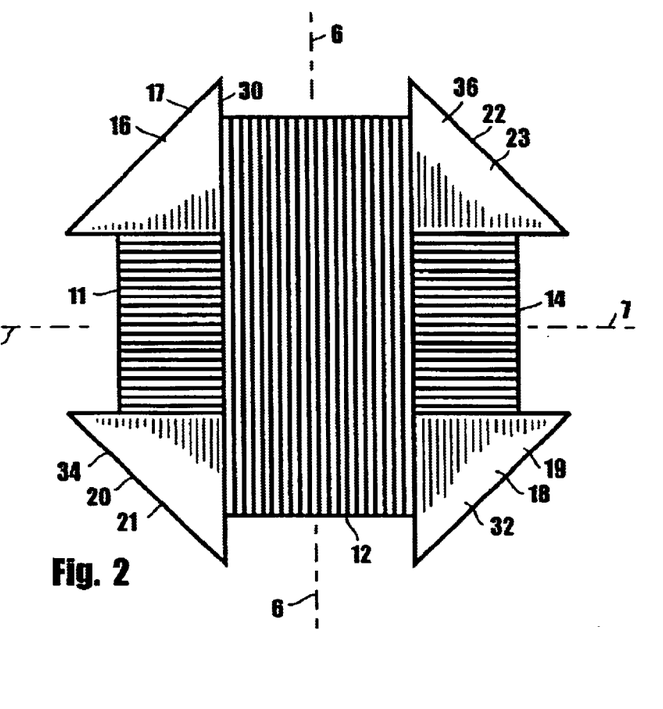
FIG. 2 top view of the front plan view of the eddy current probe coils and posts of FIG. 1.
Figure 3:
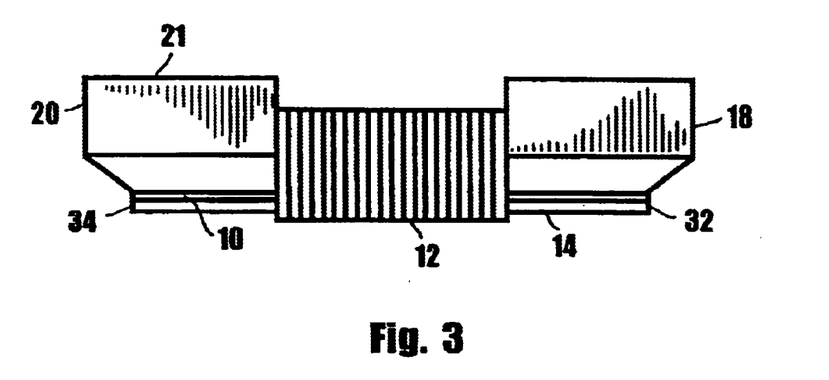
FIG. 3 is an end view of the eddy current probe coils and posts of FIG. 1.
Figure 4:
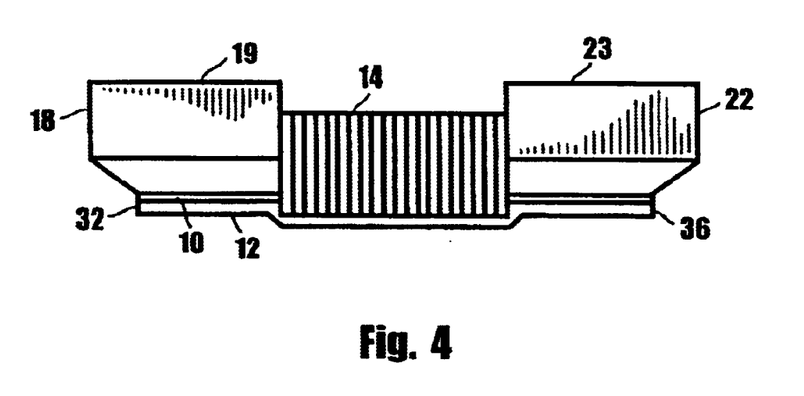
FIG. 4 is a side view of the eddy current probe coils and posts of FIG. 1.
Figure 5:
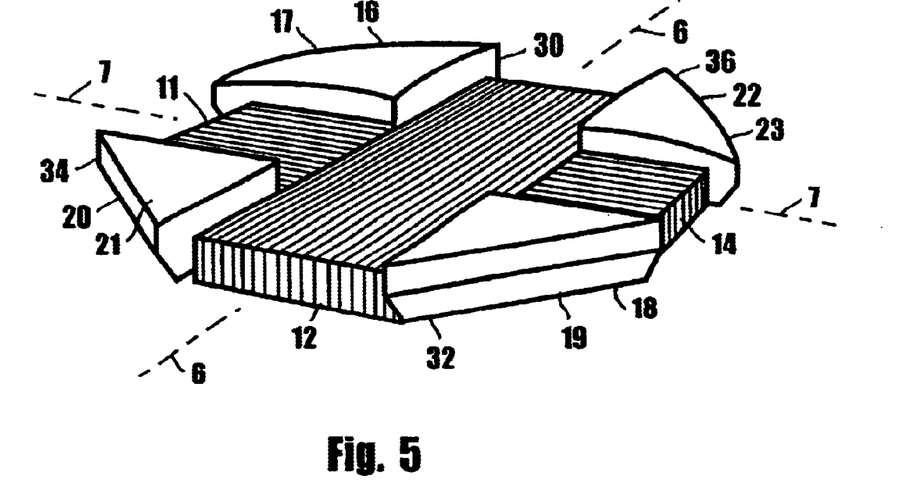
FIG. 5 is a perspective view of the eddy current probe of the present invention showing orthogonal coils wound around a common base between magnetic field directing posts on extended base corners with post ends having a rounded curvature matching that of an inner surface of a tubular material to be tested from its inside, the curvature of two adjacent post ends circumscribing a circle.
Figure 6:
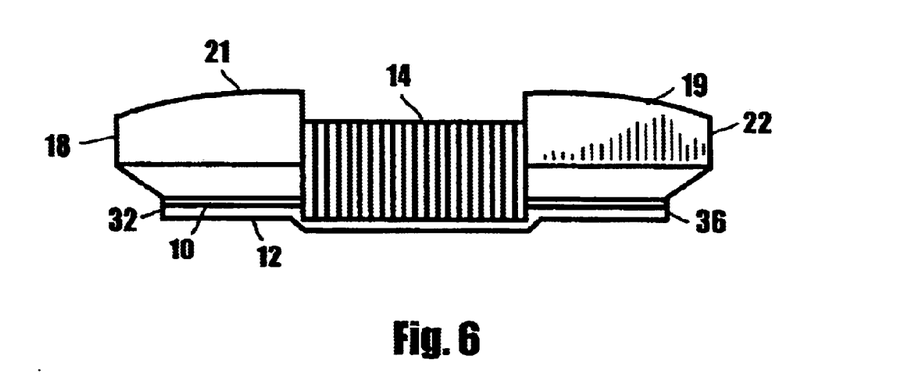
FIG. 6 is an end view of the eddy current probe coils and adjacent posts of FIG. 5 showing post ends with a circular curvature.
Figure 7:
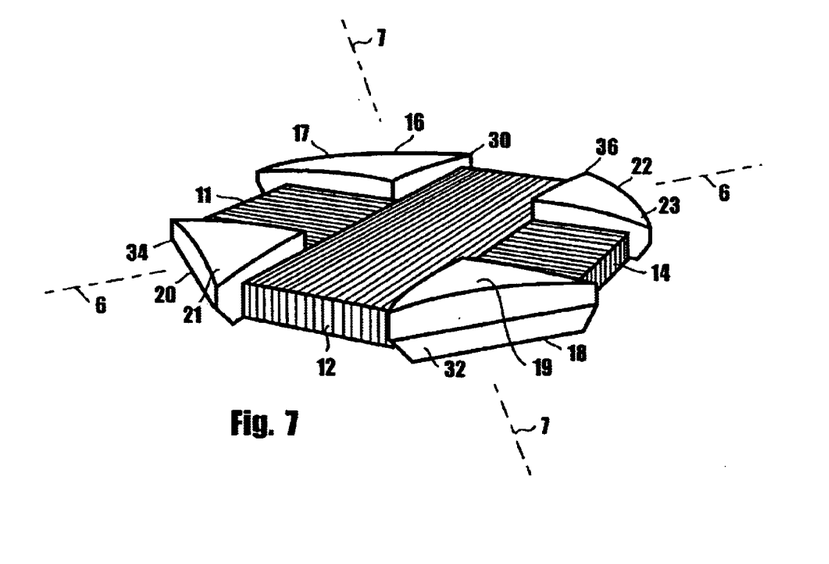
FIG. 7 is a perspective view of the eddy current probe of the present invention showing orthogonal coils wound around a common base between magnetic field directing posts on extended base corners with post ends having a rounded curvature matching that of an inner surface of a tubular material to be tested from its inside, the curvature of two diagonal central post ends circumscribing a circle in a plane transverse to a probe axis, forward and rearward post ends each circumscribing a circle of the same radius also transverse to the probe axis forward and rearward of the central post ends.
Figure 9:
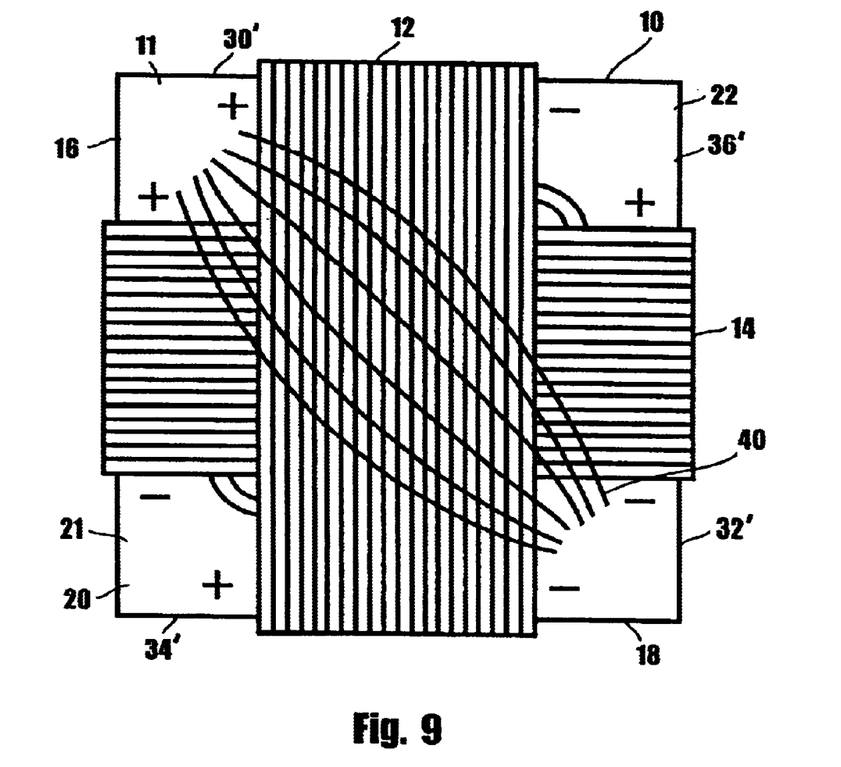
FIG. 9 is a perspective view of the eddy current probe of the present invention showing orthogonal coils wound around a common base between magnetic field directing posts on base corners within the base rectangle.
Figure 16:
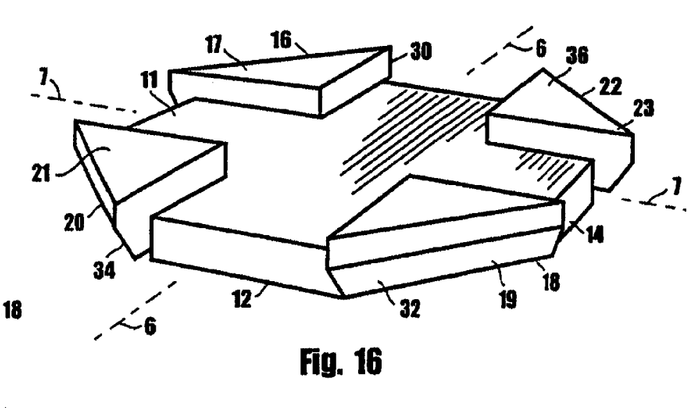
FIG. 16 is a perspective view of the base showing the base front and posts depending from the base front at its respective corners without coils wound on the base.

A coil assembly for an eddy current probe (not shown) having a longitudinal axis 6 along its direction of probe travel as shown in FIG. 5 and FIG. 7 comprises generally rectangular wafer base 10 of high permeable material, two solenoid coils 12 and 14 each with a plurality of winds in mutual orthogonal relation around the base 10, and first and second posts 16 and 18 of high permeable material respectively depending perpendicularly from the base front 11 at two base corners 30 and 32 diagonally opposed as shown in FIG. 6. FIG. 9 and FIG. 16. The posts 16 and 18 may depend from the base on corners 30 and 32 typically extending diagonally from the rectangular base 10, as shown in FIG. 1. The assembly may further comprise additional third and fourth posts 20 and 22 respectively depending from the base 10 on other base corners 34 and 36 diagonally opposed. The additional third and fourth posts 20 and 22 may also depend from the base on corners 34 and 36 also typically extending diagonally from the rectangular base 10, as shown in FIG. 1. Typically, the posts include post sides parallel to and offset from the base sides. With the posts extending from base corners, they form a channel at each base side with the post sides comprising channel sides with the respective coil winds passing within the channels.

Figure 10:
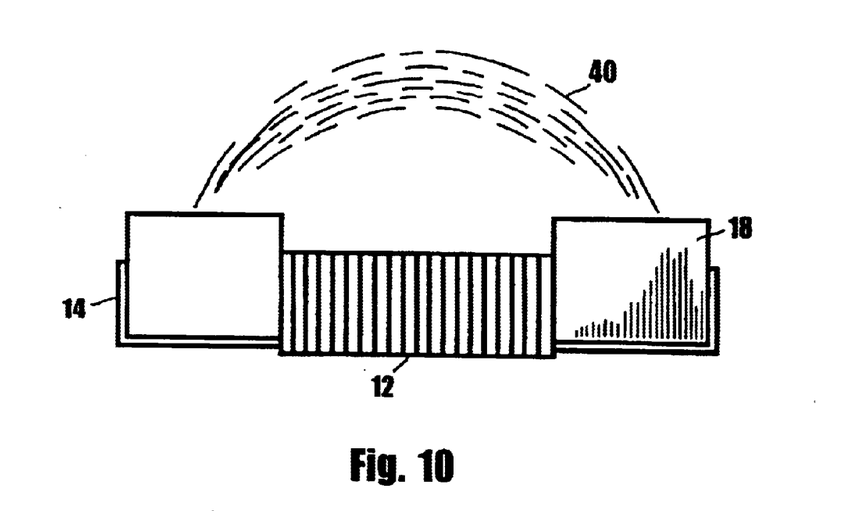
FIG. 10 is an end view of the eddy current probe coils and posts of FIG. 7 showing magnetic fields between posts extending from base corners.
Figure 11:
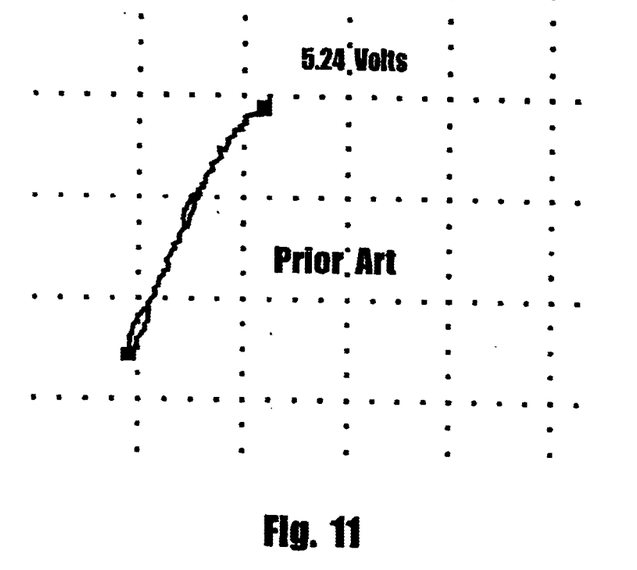
FIG. 11 is a graph showing performance of the orthogonal coils of FIG. 1 without posts depending from extended base corners showing a maximum voltage of 5.24 volts generated from eddy currents in a test material during measurement of a standard material defect.
Figure 12:
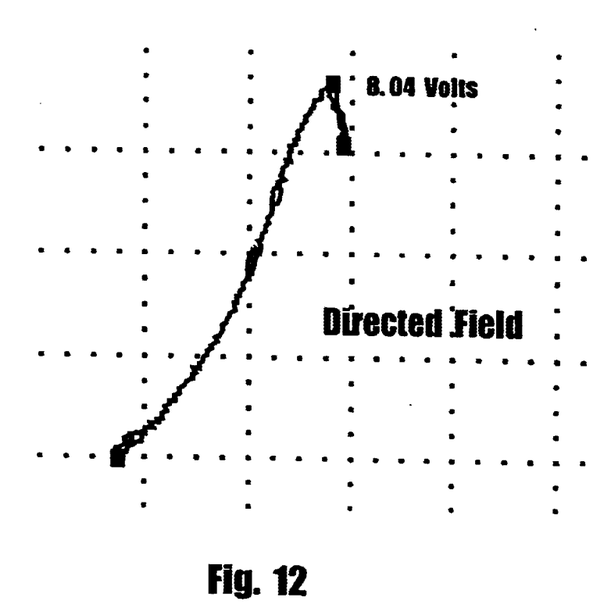
FIG. 12 is a graph showing performance of the orthogonal coils of FIG. 1 with posts depending from extended base corners showing a maximum voltage of 8.04 volts generated from eddy currents in the same test material during measurement of the same standard defect represented in the measurement of FIG. 9.
Figure 13:
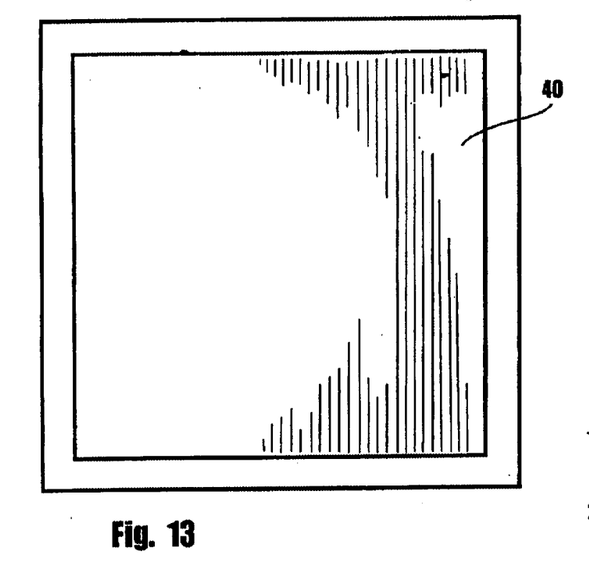
FIG. 13 is a top planar view of a coil assembly bottom cap.
Figure 14:
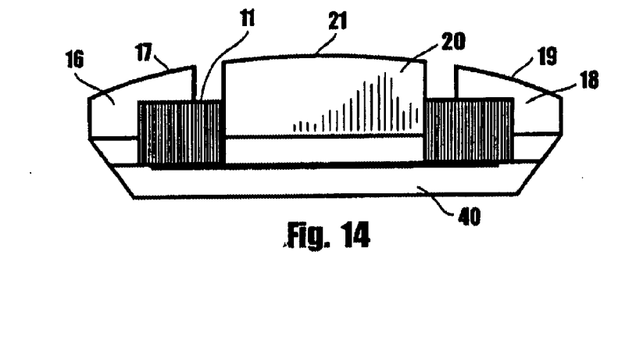
FIG. 14 is an end view of the bottom cap of FIG. 13 shown attached to the bottom of a coil assembly through which magnet fields are guided in completing a magnetic circuit under the base.
Figure 15:
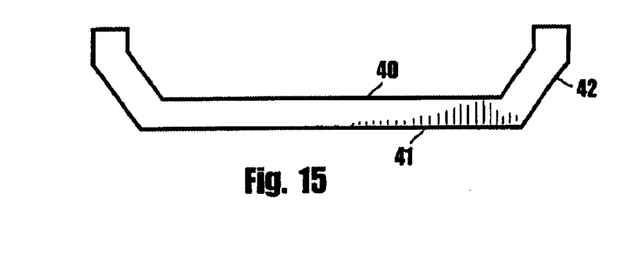
FIG. 15 is an end view of the assembly cap with sides for extending up alongside posts.

With the coils electrically connected to alternating current, the coils 12 and 14 become a solenoid with the wafer base as a common core. First diagonally opposing base corners 30 and 32 then have complementary magnetic polarities with magnetic field lines 40 going between them in completing a magnetic circuit when the alternating electric currents of the coils are in phase as shown in FIGS. 9 and 10. With posts 16 and 18 at the corners, the magnetic field lines pass through the posts, emanating from post ends 17 and 19.

Coils 12 and 14 each generate magnetic fields creating like magnetic poles with constructive interference at the first diagonally opposing base corners 30 and 32. The coils also generate complementary (unlike + and −) magnetic poles at second diagonally opposing base corners 34 and 36 and magnetic field lines simply short between them without consequence. When the alternating electric currents of the coils are connected out of phase, the second diagonally opposing base corners 34 and 36 have like magnetic polarity with magnetic field lines passing between them and the first diagonally opposing base corners 30 and 32 have complementary magnetic polarity. Thus, electrical connection to the coils typically is rapidly changed to create magnetic field lines changing from one direction to an orthogonal direction to measure material anomalies that might be dependent on orientation. In like manner, the combined magnetic field bridges through the second diagonally opposing base corners 34 and 36, passing through ends 21 and 23 of third and fourth posts 20 and 22 when the coils are electrically driven out of phase. Typically, the signals measured in the first and second coils are differenced to remove unwanted signal components leaving primarily only an eddy current signal.

Figure 8:
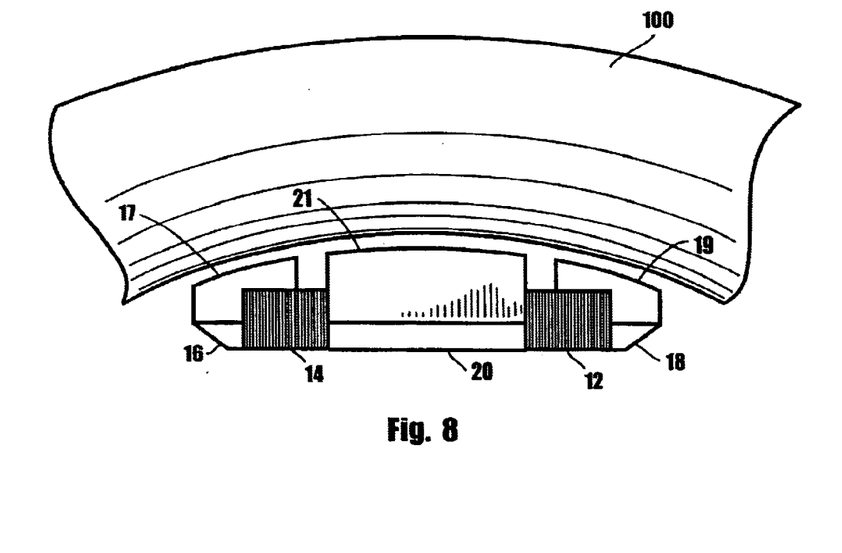
FIG. 8 is an end view of the eddy current probe coils and adjacent posts of FIG. 7 showing the rearward post end and central post ends with a same circular curvature.

FIG. 5 and FIG. 6 show adjacent post ends 19 and 21 of second and third posts 18 and 20 convex curved to match a concave material to be tested, such as an inner surface of a tubular structure 100 as shown in FIG. 8. The post end curvature is in a circular arc such that when the probe is rotated about its axis 6 normal to the plane of rotation 7 of the adjacent posts 18 and 20, the post ends 19 and 21 circumscribe a circle transverse to the probe axis of rotation 6.

FIG. 7 and FIG. 8 show diagonal post ends 17 and 19 of first and second posts 16 and 18 aligned transverse to the probe axis of rotation 6 with curvatures circumscribing portions of a same circular arc in a plane 7 transverse to the probe axis 6. Curvatures of posts 20 and 22 rearward and forward of transversely aligned posts 16 and 18 circumscribe a like circular arc with the coil assembly rotated 45 degrees from the orientation of the coil assembly shown in FIG. 5 and FIG. 6.

As shown in FIG. 9, orthogonal coils 12 and 14 may wind around a rectangular base 10 between magnetic field-directing posts 16, 18, 20, and 22 on respective base corners 30', 32', 34', and 36' that may be within the base rectangle.

Clearly, it is only advantageous to have depending posts 16 and 18 at base corners 30 and 32 where magnetic fields encounter constructive interference. As mentioned, magnetic fields loop between these corners in completing a magnetic circuit over the base and coils. Without posts depending from base corners, the magnetic field looping to the complementary corner diagonal across the base is perpendicular and close to the base. Ideally, the posts are located diagonally from the base corner approximately at that location where the field lines are perpendicular to the base, capturing the magnetic field within the posts and redirecting the field through posts and out of post ends before looping to a post at the complementary corner diagonal across the wafer base.

Though is it intended that magnetic fields generated by the coils be routed through the posts for coupling into a test material near post ends, completing the magnetic circuit between diagonal post ends, secondary magnetic fields will also escape the posts and complete its circuit under the assembly base instead of over the base through post ends. As shown in FIGS. 9–15, to To capture these secondary field lines and guide them close to the base between wafer corners, a cap 50 of high permeability material may be fit between the base corners, therein capturing these secondary field lines to better define and complete the magnetic circuit. Thus, extraneous affects that may derive from these secondary fields are minimized or eliminated. In practice, the cap may be a plate 51 covering the entire underside of the base and coils. The cap may extend from under the base up alongside the posts and/or coils with cap sides 52 or simply remain a flat plate under the base between the corners. The cap may be in noncontact with the base corners or posts such that the fields are principally directed from the base into the posts rather than the cap, the cap being near the posts to capture secondary field lines that might escape the posts.

Having described the invention, what is claimed is as follows:

1. A coil assembly for an eddy current probe comprising
   a base,
   a post of high permeability material at each of two base corners diagonally opposed,
   a first coil around the base having a plurality of winds around first opposing sides of the base, adapted to be connected to a first source of alternating electric current in generating a first magnetic field,
   a second coil around the base orthogonal to and crossing the first coil also having a plurality of winds around second opposing sides of the base separated by said first opposing sides, also adapted to be connected to a source of alternating electrical current in generating a second magnetic field,
   wherein the magnetic fields have like poles at the two diagonally opposing base corners, the two magnetic fields combining at said two diagonally opposing base corners.

2. The coil assembly of claim 1 further comprising a cap adapted to fit under the base and between posts at base corners.

3. The coil assembly of claim 2 further comprising cap sides sized to fit around posts at base corners.

4. The coil assembly of claim 1 wherein respective post ends have a curvature matching a curvature of a material to be tested such that the post ends when disposed close to said material with a curvature is approximately in equidistant proximity to the material throughout each post end, therein better coupling said magnetic fields from said post ends into said material.

5. The coil assembly of claim 4 wherein said respective post ends are convex to match a concave curvature of said material to be tested.

6. The coil assembly of claim 4 wherein said respective post ends have a curvature matching a portion of a cylindrical inner surface.

7. The coil assembly of claim 4 wherein said respective post ends are flat matching a flat surface to be tested.

8. The coil assembly of claim 1 further comprising third and fourth posts of high permeability material at two additional diagonally opposed base corners, the coils around the base passing between respective posts at base corners.

9. The coil assembly of claim 8 wherein ends of first and third posts comprise front adjacent posts transverse to a probe axis of rotation lying in a probe direction of forward translation and ends of second and fourth posts comprise rear adjacent posts also transverse to a probe axis of rotation lying in a probe direction of forward translation, and wherein front adjacent posts trace a first circular path when the probe is rotated about its axis as the rear adjacent posts trace a second circular path rearward of the first circular path.

10. The coil assembly of claim 8 wherein first and second posts comprise transverse posts aligned in a central plane transverse to the probe axis and third and fourth posts comprise longitudinal post aligned parallel with the probe axis, and wherein the first and second posts are adapted to rotate in said plane transverse to the probe axis with ends of said first and second posts circumscribing a circular path about said probe and wherein said third and fourth posts rotate in forward and rearward planes, respectively, transverse to said probe axis respectively forward and rearward of the central plane with ends of said third and fourth posts each circumscribing a circular path about said probe in its respective plane.

11. The coil assembly of claim 1 wherein signals measured at said first and second coils are differenced to remove unwanted signal components common to both coils.

12. The coil assembly of claim 1 wherein said first coil and second coils are alternately electrically connected first in phase producing like magnetic poles at the two diagonally opposing base corners with a first diagonal magnetic field bridging between them diagonally across the base and then second 180 degrees out of phase producing like magnetic poles at the two additional base corners diagonally opposed with a second diagonal magnetic field orthogonal to the first magnetic field then bridging between the two additional base corners diagonally across the base, said magnetic fields guided through the posts and emanating from respective post ends at the respective base corners.

13. The coil assembly of claim 12 wherein signals measured at said first and second coils are differenced sequentially with the coils first in phase and then out of phase to remove unwanted signal components common to both coils with the magnetic fields in each of the orthogonal orientations.

14. The coil assembly of claim 1 wherein the post at each of two base corners comprises first and second posts at said two diagonally opposed base corners, respectively, depending perpendicularly from a base front, said magnet fields guided through the two posts and emanating from respective post ends.

15. A coil assembly for an eddy current probe comprising
   a base,
   at least four posts of high permeability material extending upward from the base,
   a plurality of coils around the base each wound between a different pair of said posts resulting in unaligned coils, each of said coils adapted to be connected to alternating electric current in generating a magnetic field wherein two of said magnetic fields have like poles at two or more posts, the two magnetic fields combining at said two or more posts and being guided through the posts, emerging therefrom at post ends.

16. For a coil assembly for an eddy current probe including a base, at least four posts of high permeability material extending upward from the base, a plurality of coils around the base each wound between a different pair of said posts resulting in unaligned coils, the method of generating magnetic fields of different orientation adapted to couple into a test material for generating eddy currents in the material at said different orientations therein better discovering material flaws more perceptible at one orientation that another orientation, comprising the following steps:

(1) Connecting electric current to said coils therein generating magnetic fields wherein said magnetic fields have like poles at a first two posts, the two magnet fields combining at said first two posts being guided through the posts and emerging therefrom at post ends resulting in a single first combined magnetic field between said post ends;

(2) Detecting a first return magnetic field generated by eddy currents in said material;

(3) Connecting electric current to said coils therein generating magnetic fields wherein said magnetic fields have like poles at a second two posts, the two magnet fields combining at said second two posts being guided through the posts and emerging therefrom at post ends resulting in a single second combined magnetic field between said post ends;

(4) Detecting a second return magnetic field generated by eddy currents in said material at an orientation different from eddy currents generating said first return magnetic field due to different orientations of said first and second combined magnetic fields;

(5) Differencing signals generated by said first and second return magnetic fields;

(6) Moving the coil assembly along the test material while repeating steps (1) through (5).

\* \* \* \* \*